(12) United States Patent
Chen et al.

(10) Patent No.: US 12,201,840 B2
(45) Date of Patent: Jan. 21, 2025

(54) ELECTRICAL STIMULATION DEVICE AND METHOD

(71) Applicant: Industrial Technology Research Institute, Hsinchu (TW)

(72) Inventors: Kuo-Tso Chen, Taipei (TW); Yen-Chung Huang, Zhudong Township (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 914 days.

(21) Appl. No.: 17/135,108

(22) Filed: Dec. 28, 2020

(65) Prior Publication Data
US 2022/0203090 A1  Jun. 30, 2022

(51) Int. Cl.
*A61N 1/36* (2006.01)
*H02M 3/07* (2006.01)
*H02M 1/00* (2006.01)

(52) U.S. Cl.
CPC ....... *A61N 1/3614* (2017.08); *A61N 1/36125* (2013.01); *A61N 1/36153* (2013.01);
(Continued)

(58) Field of Classification Search
CPC .............. A61N 1/0507; A61N 1/0534; A61N 1/36062; A61N 1/36067; A61N 1/3614; A61N 1/36125; A61N 1/36153; A61N 1/36157; H02M 1/007; H02M 1/0077; H02M 1/0087; H02M 3/07; H02M 3/073; H02M 7/5387
(Continued)

(56) References Cited

U.S. PATENT DOCUMENTS 7,697,992 B2  4/2010  Voelkel
8,150,518 B2  4/2012  Levin et al.
(Continued)

FOREIGN PATENT DOCUMENTS

CN  101510730 B  12/2011
CN  103052424 A  4/2013
(Continued)

OTHER PUBLICATIONS

Chen et al., "A Fully Integrated 8-Channel Closed-Loop Neural-Prosthetic CMOS SoC for Real-Time Epileptic Seizure Control," IEEE Journal of Solid-State Circuits, vol. 49, No. 1, Jan. 2014 (Date of publication Oct. 18, 2013), pp. 232-247.
(Continued)

*Primary Examiner* — Pamela M. Bays
(74) *Attorney, Agent, or Firm* — Birch, Stewart, Kolasch & Birch, LLP (57) ABSTRACT

An electrical stimulation device is provided. The electrical stimulation device includes a boost circuit, a voltage selecting circuit and a control circuit. The boost circuit generates a plurality of voltages, wherein the voltages have different voltage values. The voltage selecting circuit is coupled to the boost circuit and selects one voltage according to a reference voltage on a tissue impedance to generate an output voltage. The control circuit is coupled to the boost circuit and in response to electrical stimulation; it transmits a control signal to enable the boost circuit.

22 Claims, 9 Drawing Sheets

(52) U.S. Cl.
CPC ......... *A61N 1/36157* (2013.01); *H02M 1/007* (2021.05); *H02M 1/0077* (2021.05); *H02M 3/07* (2013.01)

(58) Field of Classification Search
USPC .......................................................... 607/62
See application file for complete search history.

(56) References Cited

U.S. PATENT DOCUMENTS

| | | | |
|---|---|---|---|
| 8,290,583 | B2 | 10/2012 | Vernon et al. |
| 8,463,390 | B2 | 6/2013 | Muraoka |
| 9,101,767 | B2 | 8/2015 | Trier et al. |
| 9,174,051 | B2 | 11/2015 | Marnfeldt et al. |
| 9,233,254 | B2 | 1/2016 | Nimmagadda et al. |
| 9,855,429 | B2 | 1/2018 | Cowan |
| 10,307,595 | B2 | 6/2019 | Shi et al. |
| 10,525,252 | B2 | 1/2020 | Feldman et al. |
| 10,589,090 | B2 | 3/2020 | Feldman et al. |
| 2015/0025352 | A1 | 1/2015 | Caytak et al. |
| 2020/0406033 | A1* | 12/2020 | Loh ................... A61N 1/36007 |
| 2022/0233866 | A1* | 7/2022 | Gururaj ............. A61N 1/36146 |

FOREIGN PATENT DOCUMENTS

| | | |
|---|---|---|
| CN | 105120945 A | 12/2015 |
| CN | 104254368 B | 3/2017 |
| CN | 208130251 U | 11/2018 |
| CN | 106456978 B | 1/2019 |
| CN | 209790616 U | 12/2019 |
| CN | 111053975 A | 4/2020 |
| CN | 211188787 U | 8/2020 |
| CN | 211536220 U | 9/2020 |
| TW | I235523 B | 7/2005 |
| TW | I306407 B | 2/2009 |
| TW | 201325648 A1 | 7/2013 |
| TW | 201442759 A | 11/2014 |
| TW | I513484 B | 12/2015 |
| TW | 201842945 A | 12/2018 |
| TW | 201828871 A | 7/2019 |

OTHER PUBLICATIONS

Lin et al., "A Battery-Less, Implantable Neuro-Electronic Interface for Studying the Mechanisms of Deep Brain Stimulation in Rat Models," IEEE Transactions on Biomedical Circuits and Systems, vol. 10, No. 1. Feb. 2016 (Date of publication Mar. 31, 2015), pp. 98-112.

Taiwanese Office Action and Search Report for Taiwanese Application No. 109146450, dated Aug. 9, 2021.

Taiwanese Office Action and Search Report for Taiwanese Application No. 109146450, dated Dec. 28, 2021.

* cited by examiner

ELECTRICAL STIMULATION DEVICE AND METHOD

TECHNICAL FIELD

The disclosure generally relates to electrical stimulation technology, and more particularly, to an electrical stimulation technology in which a voltage selecting circuit is used to select an output voltage automatically according to a reference voltage on the tissue impedance.

BACKGROUND

As technology has progressed, the electrical stimulation device can be applied in more implantable medical technologies, such as Deep Brain Stimulation (DBS), Cranial Electrotherapy Stimulation (CES), spinal cord electrical-stimulation, gastrointestinal electrical-stimulation, sacral nerve electrical-stimulation, and so on.

Because the electrical stimulation device needs to be implanted into the human body, smaller volume, a longer charge period and lower power consumption will become very important requirements for the application of the electrical stimulation device.

BRIEF SUMMARY

An electrical stimulation device and method are provided to overcome the problems described above.

An embodiment of the disclosure provides an electrical stimulation device. The electrical stimulation device comprises a boost circuit, a voltage selecting circuit and a control circuit. The boost circuit generates a plurality of voltages, wherein the voltages have different voltage values. The voltage selecting circuit is coupled to the boost circuit and selects one of the voltages according to a reference voltage on a tissue impedance to generate an output voltage. The control circuit is coupled to the boost circuit and in response to electrical stimulation, it transmits a control signal to enable the boost circuit.

In some embodiments, the electrical stimulation device further comprises a first switch circuit and a second switch circuit. The first switch circuit comprises a first switch and a second switch, wherein the first switch and the second switch are coupled to a first electrode input end and a second electrode input end respectively. The second switch circuit comprises a third switch and a fourth switch, wherein the third switch and the fourth switch are coupled to the first electrode input end and the second electrode input end respectively. In some embodiments, the control circuit controls the enabling and disabling of the first switch and the second switch to control the transformation between a positive voltage and a negative voltage.

In some embodiments, the voltage selecting circuit detects the reference voltage through the first electrode input end or the second electrode input end, wherein the first electrode input end is coupled to one end of the tissue impedance and the second electrode input end is coupled to the other end of the tissue impedance.

In some embodiments, electrical stimulation device comprises a first diode and a second diode. The first diode is coupled to an adjustable current source and the first switch. The second diode is coupled to the adjustable current source and the third switch. When the first switch is enabled, the first diode is coupled to the first electrode input end to transmit the reference voltage to the voltage selecting circuit, and when the third switch is enabled, the second diode is coupled to the second electrode input end to transmit the reference voltage to the voltage selecting circuit.

In some embodiments, the boost circuit comprises a plurality of stages of charge pump circuits and a plurality of capacitors, wherein the stages of the charge pump circuits generate voltages according to the control signal and the capacitors are configured to store the respective voltages.

In some embodiments, the voltage selecting circuit comprises a plurality of stages of the selecting circuits, wherein the stages of the selecting circuits correspond to the respective voltages.

In some embodiments, each stage of the selecting circuit comprises a diode, a first Zener diode and a first transistor. The diode is coupled to the boost circuit. A first drain of the first transistor is coupled to the diode, a first source of the first transistor is coupled to one end of the first Zener diode, and a first gate of the first transistor is coupled to the other end of the first Zener diode.

In some embodiments, except for the first stage, each stage of the selecting circuits further comprises a second Zener diode and a second transistor. The second source of the second transistor is coupled to one end of the second Zener diode, and a second gate of the second transistor is coupled to the other end of the second Zener diode. In some embodiments, the first stage of the selecting circuit further comprises a first resistor and a second resistor, wherein one end of the first resistor is coupled to a first diode and a second diode, and the other end of the first resistor is coupled to a current source and one end of the second resistor is coupled to the current source, and the other end of the second resistor is coupled to the first Zener diode and the first gate of the first transistor. In some embodiments, except for the first stage, each stage of the selecting circuits further comprises a first resistor and a second resistor, one end of the first resistor is coupled to the first drain of the first transistor of the prior stage of the selecting circuit and the diode, and the other end of the first resistor is coupled to the second Zener diode and the second gate of the second transistor; and wherein one end of the second resistor is coupled to a current source, and the other end of the second resistor is coupled to a second drain of the second transistor.

In some embodiments, the first gate of the first transistor and the second drain of the second transistor are coupled to one end of the first Zener diode, and the first source of the first transistor and the second source of the second transistor are coupled to the other end of the first Zener diode.

In some embodiments, when the diode is forward biased, the first transistor is enabled and the second transistor is disabled, the selecting circuit outputs the output voltage based on its corresponding voltage.

An embodiment of the disclosure provides an electrical stimulation method. The electrical stimulation method is applied to an electrical stimulation device. The electrical stimulation method comprises the steps of using a control circuit of the electrical stimulation device to transmit a control signal to enable a boost circuit of the electrical stimulation device in response to electrical stimulation; using the boost circuit to generate a plurality of voltages, wherein the voltages have different voltage values; and using a voltage selecting circuit of the electrical stimulation device to select one voltage according to a reference voltage on a tissue impedance to generate an output voltage.

Other aspects and features of the disclosure will become apparent to those with ordinary skill in the art upon review of the following descriptions of specific embodiments of electrical stimulation device and method.

BRIEF DESCRIPTION OF THE DRAWINGS

The disclosure will become more fully understood by referring to the following detailed description with reference to the accompanying drawings, wherein.

DETAILED DESCRIPTION

The following description is of the best-contemplated mode of carrying out the disclosure. This description is made for the purpose of illustrating the general principles of the disclosure and should not be taken in a limiting sense. The scope of the disclosure is best determined by reference to the appended claims.

Figure 1:
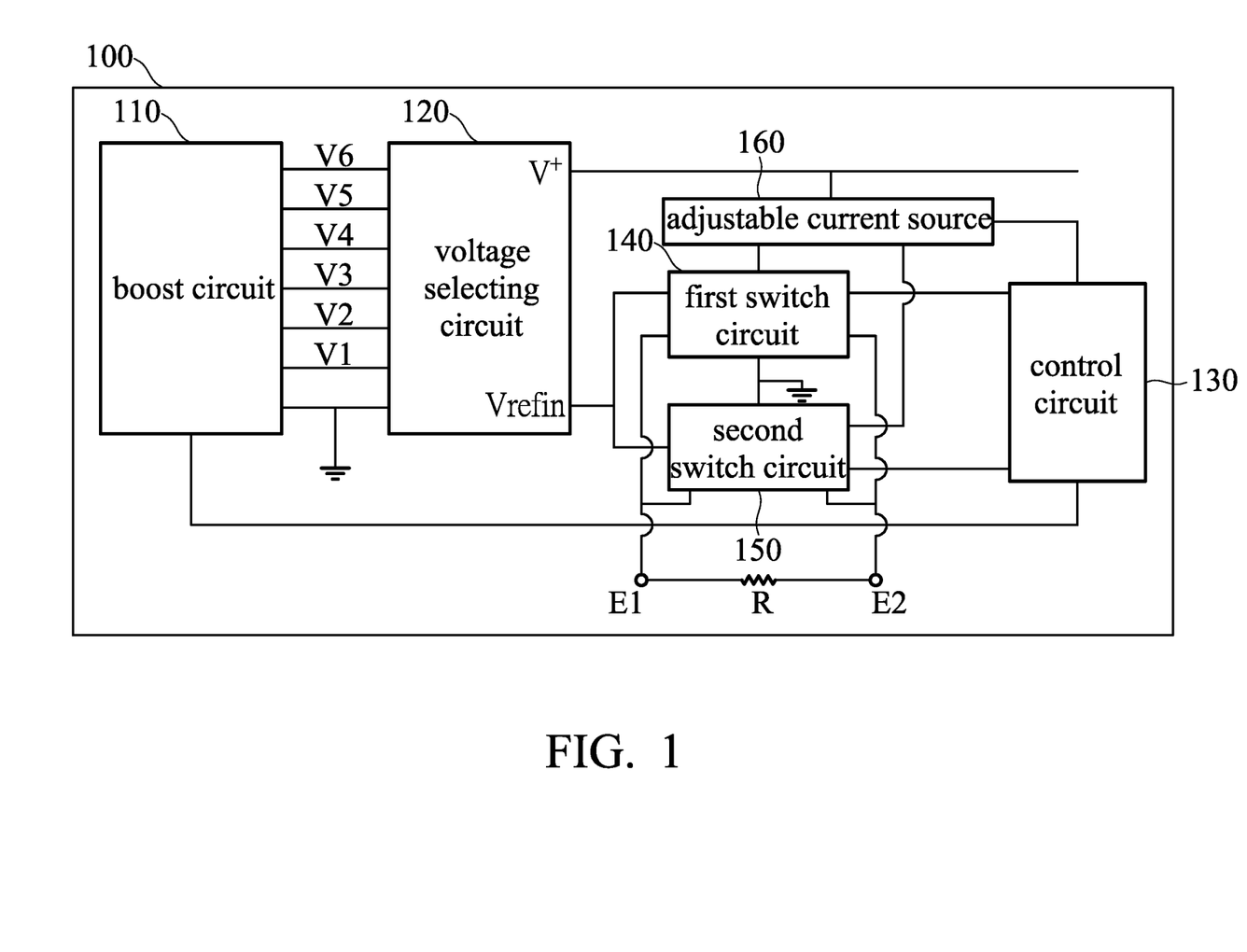
FIG. 1 is a block diagram of an electrical stimulation device 100 according to an embodiment of the disclosure.

FIG. 1 is a block diagram of an electrical stimulation device 100 according to an embodiment of the disclosure. As shown in FIG. 1, the electrical stimulation device 100 may comprise a boost circuit 110, a voltage selecting circuit 120, control circuit 130, a first switch circuit 140, a second switch circuit 150 and an adjustable current source 160. It should be noted that FIG. 1 presents a simplified block diagram in which only the elements relevant to the disclosure are shown. However, the disclosure should not be limited to what is shown in FIG. 1. The electrical stimulation device 100 may also comprise other elements and devices.

According to embodiments of the disclosure, the boost circuit 110 may be configured to generates a plurality of voltages V1~V6 to provide the voltage selecting circuit 120 with selecting. The structure of the boost circuit 110 is illustrated based on FIGS. 2A-2B below.

According to embodiments of the disclosure, according to a reference voltage, the voltage selecting circuit 120 may select a suitable voltage from the voltages generated by the boost circuit 110, and the selected voltage will be taken as an output voltage V+. The structure of the voltage selecting circuit 120 is illustrated based on FIG. 3 below.

According to embodiments of the disclosure, the control circuit 130 may control the boost circuit 110, the first switch circuit 140, the second switch circuit 150 and the adjustable current source 160 according to commands from an external device (not shown in figures). The control circuit 130 may control enabling or disabling of the first switch circuit 140 and the second switch circuit 150 to control the transformation between the positive voltage and the negative voltage. In addition, when the electrical stimulation is performed, the control circuit 130 may transmit a control signal Vc to enable the boost circuit 110. The structure of the control circuit 130 is illustrated based on FIGS. 2A-2B and FIG. 3 below.

According to embodiments of the disclosure, the first switch circuit 140 may be coupled to a first electrode input end E1 and a second electrode input end E2, and the second switch circuit 150 may be coupled to the first electrode input end E1 and the second electrode input end E2. When the first switch circuit 140 is enabled, the first switch circuit 140 may obtain the reference voltage Vrefin on the tissue impedance R (e.g. the independence of the human body or biological tissue) from the first electrode input end E1 and the second electrode input end E2. When the second switch circuit 150 is enabled, the second switch circuit 150 may obtain the reference voltage Vrefin on the tissue impedance R from the first electrode input end E1 and the second electrode input end E2.

Figure 2A:
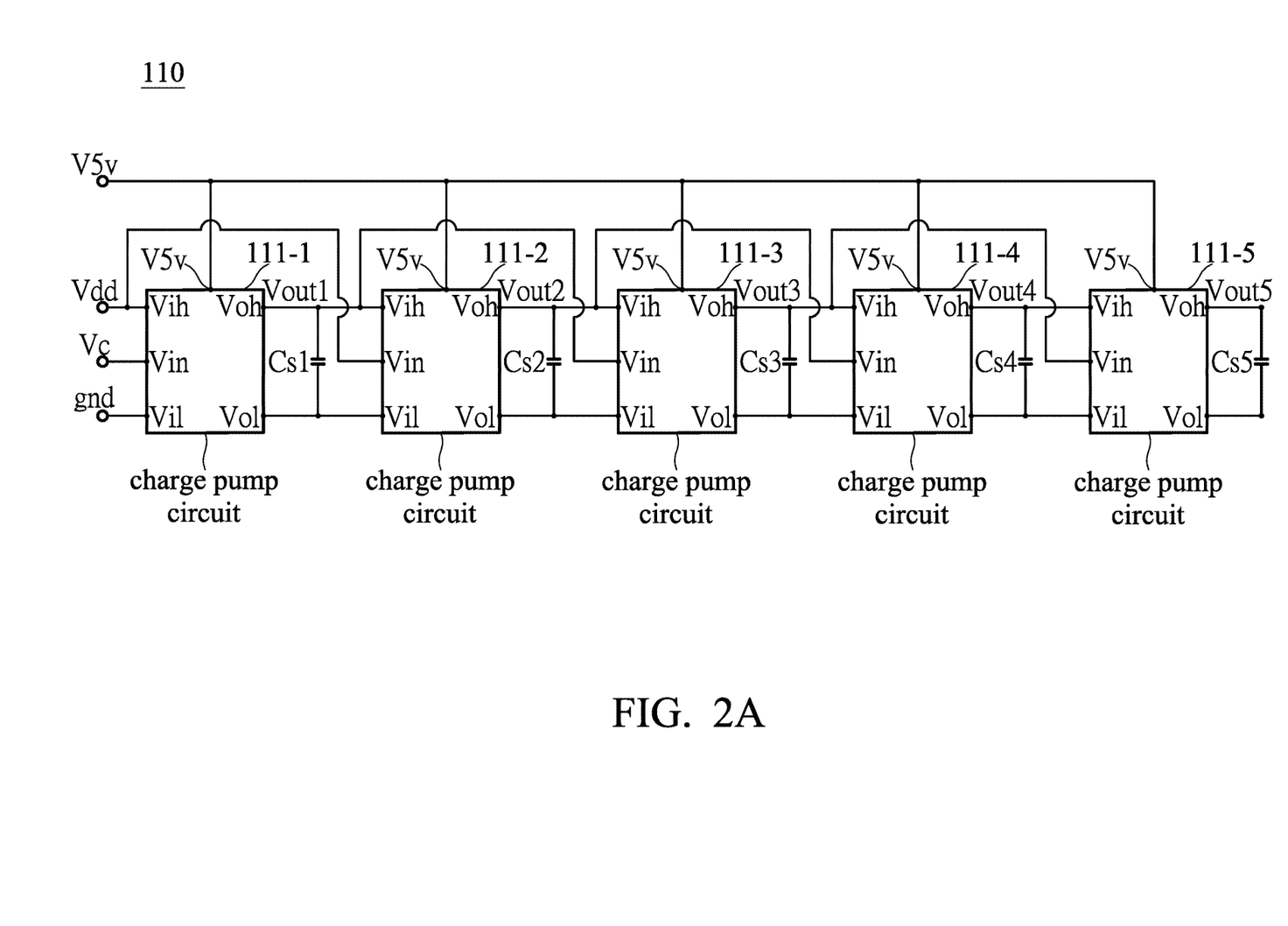
FIG. 2A is a circuit diagram of a boost circuit 110 according to an embodiment of the disclosure.

FIG. 2A is a circuit diagram of a boost circuit 110 according to an embodiment of the disclosure. As shown in FIG. 2A, the boost circuit 110 may comprise a plurality of stages of the charge pump circuits 111-1~111-5 and a plurality of capacitors Cs1~Cs5. Each charge pump circuit may be corresponded to a capacitor, and each capacitor may store may store different voltage. In FIG. 2A, the V5v pin of each charge pump circuit is used to receive the 5V (the disclosure should not be limited thereto) voltage from the battery (not shown in figures) of the electrical stimulation device 100. The Vih pin of each charge pump circuit is used to receive the output of the Voh pin of the prior stage of charge pump circuit, wherein the Vih pin of the first stage of charge pump circuit 111-1 receives the source voltage Vdd. The Vil pin of each charge pump circuit is used to receive the output of the Vol pin of the prior stage of charge pump circuit, wherein the Vil pin of the first stage of charge pump circuit 111-1 receive the ground voltage gnd. In addition, the Vin pin of the first stage of charge pump circuit 111-1 is used to receive the control signal Vc from the control circuit 130 (i.e. when the electrical stimulation is performed, the control circuit 130 may transmit the control signal Vc to the boost circuit 110), and the Vin pins of other charge pump circuits 111-2~111-5 may receive the signal received by the Vih pin of prior stage of charge pump circuit. As shown in FIG. 1, in the embodiment, the boost circuit 110 may generate the voltage V1 with 5V voltage value (i.e. the 5V voltage (not boosted) of the V5v pin=V1), the voltage V2 with 10V voltage value (i.e. the voltage of output node Vout1=V2), the voltage V3 with 15V voltage value (i.e. the voltage of output node Vout2=V3), the voltage V4 with 20V voltage value (i.e. the voltage of output node Vout3=V4), the voltage V5 with 25V voltage value (i.e. the voltage of output node Vout4=V5) and the voltage V6 with 30V voltage value (i.e. the voltage of output node Vout5=V6), but the disclosure should not be limited thereto. The voltage V1 may be outputted to the voltage selecting circuit 120 through the V5v pin of charge pump circuit. The voltages V2~V6 which are boosted may be stored in the capacitors Cs1~Cs5 respectively. The voltages V2~V6 which are boosted by the boost circuit 110 may be outputted to the voltage selecting circuit 120 through output nodes Vout1~Vout5 respectively. The operations of each charge pump circuit shown in FIG. 2A are illustrated based on FIG. 2B. It should be noted that FIG. 2A shows five stages of the charge pump circuits, but the disclosure should not be limited thereto. In other embodiments, the boost circuit 110 may also adopt different stages of the charge pump circuits. In addition, it should be noted that the boost circuit 110 shown in FIG. 2A is only an embodiment of the disclosure, but the disclosure should not be limited thereto. In other embodiments, other boost circuits also can be adopted as the boost circuit 110.

Figure 2B:
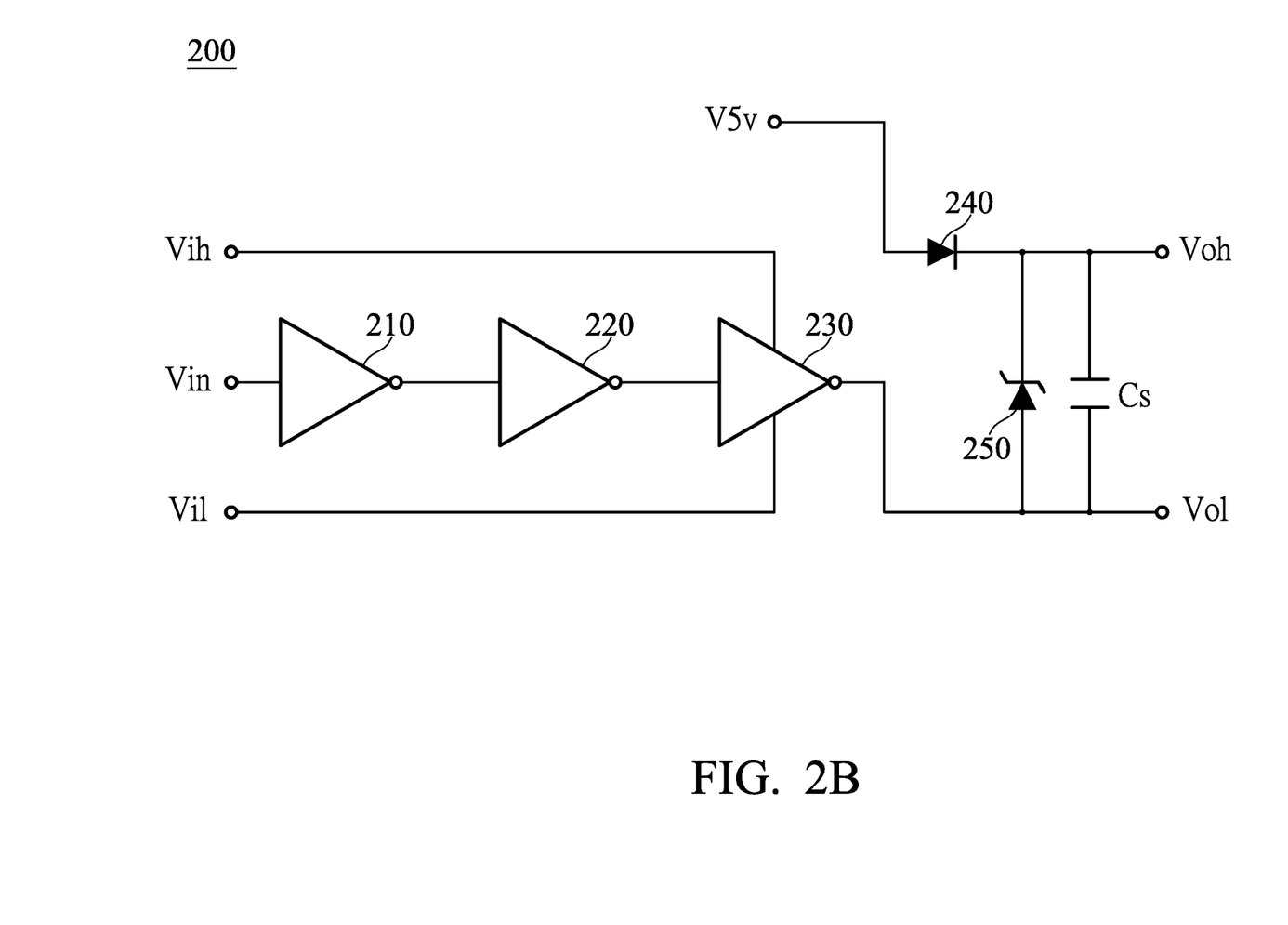
FIG. 2B is a circuit diagram of a charge pump circuit 200 according to an embodiment of the disclosure.

FIG. 2B is a circuit diagram of a charge pump circuit 200 according to an embodiment of the disclosure. The charge pump circuit 200 shown in FIG. 2B can be applied to the charge pump circuits 111-1~111-5 shown in FIG. 2A. As shown in FIG. 2B, the charge pump circuit 200 may comprise invertors 210~230, a diode 240 and a Zener diode 250. The charge pump circuit 200 may be coupled to a capacitor Cs and connected to the Zener diode 250 in parallel. In the embodiment, it is assumed that the V5v pin of the charge pump circuit 200 receives 5V voltage from the battery (not shown in figures) of the electrical stimulation device 100, the Vih pin of the charge pump circuit 200 receives 5V voltage, and the Vil pin of the charge pump circuit 200 receives 0V voltage. Therefore, when the control signal Vc received by the Vin pin of the charge pump circuit 200 is at high level (5V), the Voh pin of the charge pump circuit 200 may output 5V voltage and the Vol pin of the charge pump circuit 200 may output 0V voltage; and when the control signal Vc received by the Vin pin of the charge pump circuit 200 is at low level (0V), the Voh pin of the charge pump circuit 200 may output 10V voltage and the Vol pin of the charge pump circuit 200 may output 5V voltage. That is to say, when the control signal Vc received by the Vin pin of the charge pump circuit 200 is at low level (0V), the output voltage of the Voh pin of the charge pump circuit 200 will be twice as the voltage (i.e. 5V voltage) of the Vih pin of the charge pump circuit 200 (i.e. the voltage boost is performed), and the capacitor Cs may store the 10V of output voltage of the Voh pin of the charge pump circuit 200. On the contrary, when the control signal Vc received by the Vin pin of the charge pump circuit 200 is at high level (5V), the output voltage of the Voh pin of the charge pump circuit 200 will maintain 5V voltage (i.e. the voltage boost is not performed). In addition, in the embodiment, the Zener diode 250 is used to limit the cross-voltage between the two ends of the capacitor Cs to below 5V in order to protect the inputs (i.e. Vih pin and Vil pin) of the next stage of charge pump. It should be noted that in FIG. 2B, the charge pump circuit 200 comprises three inverters, but the disclosure should not be limited thereto. In other embodiments, the charge pump circuit 200 may comprise different number of inverters.

Figure 3:
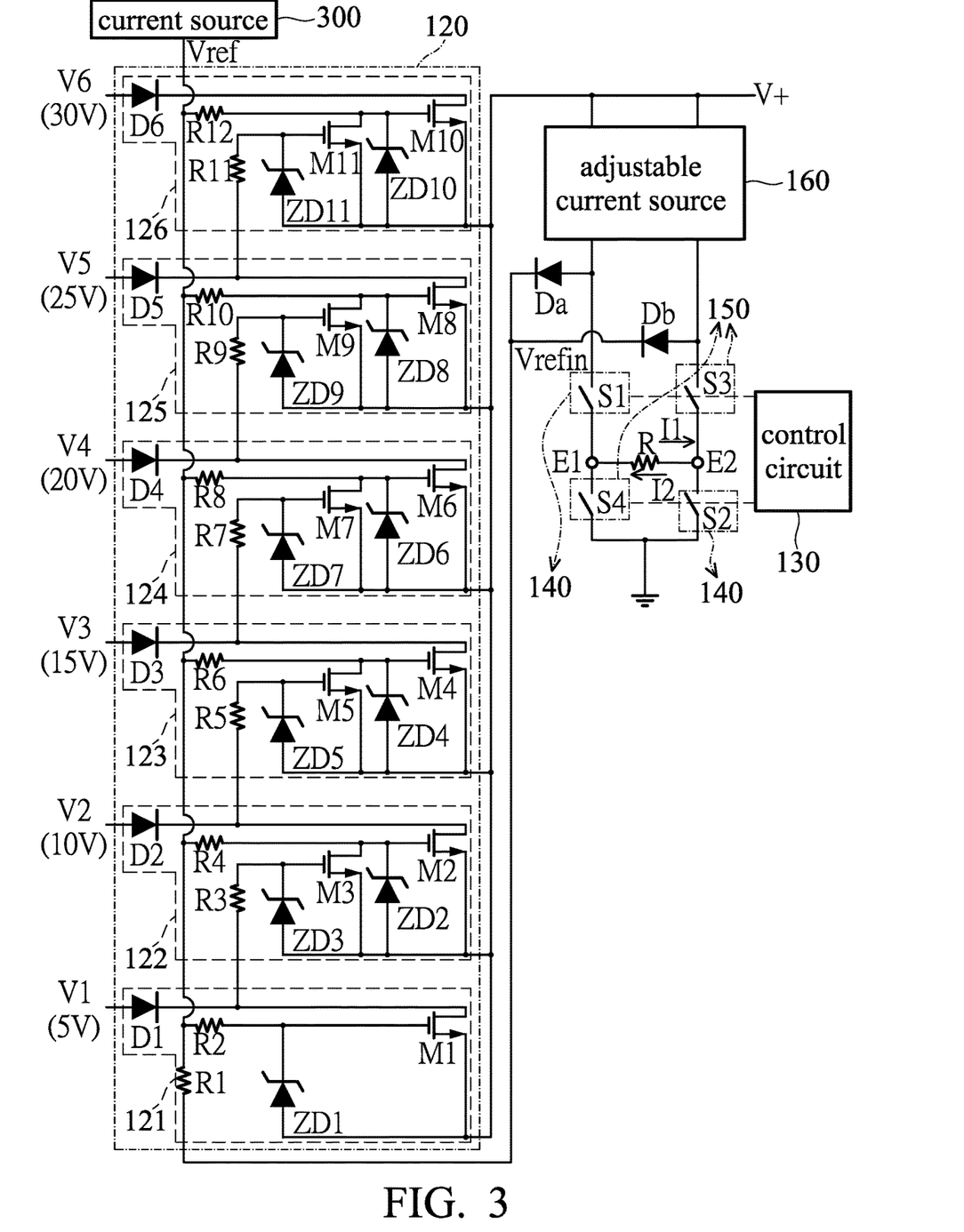
FIG. 3 is a circuit diagram of a voltage selecting circuit 120, a control circuit 130, a first switch circuit 140, a second switch circuit 150 and an adjustable current source 160 according to an embodiment of the disclosure.

FIG. 3 is a circuit diagram of a voltage selecting circuit 120, a control circuit 130, a first switch circuit 140, a second switch circuit 150 and an adjustable current source 160 according to an embodiment of the disclosure. As shown in FIG. 3, the voltage selecting circuit 120 may be coupled to a current source 300 and the voltage selecting circuit 120 may comprise a first selecting circuit 121, a second selecting circuit 122, a third selecting circuit 123, a fourth selecting circuit 124, a fifth selecting circuit 125 and a sixth selecting circuit 126. The first selecting circuit 121, the second selecting circuit 122, the third selecting circuit 123, the fourth selecting circuit 124, the fifth selecting circuit 125 and the sixth selecting circuit 126 are respectively corresponded to the voltages V1~V6 generated by the boost circuit 110. The first selecting circuit 121 may comprise a first diode D1, a first resistor R1, a second resistor R2, a first Zener diode ZD1 and a first transistor M1. One end of the first resistor R1 is coupled to the diode Da and the diode Db, and the other end of the first resistor R1 is coupled to the current source 300. One end of the resistor R2 is coupled to the current source 300, and the other end of the resistor R2 is coupled to the cathode of the first Zener diode ZD1 and the gate of the first transistor M1.

The second selecting circuit 122 may comprise a second diode D2, a third resistor R3, a fourth resistor R4, a second Zener diode ZD2, a third Zener diode ZD3, a second transistor M2 and a third transistor M3. One end of the third resistor R3 is coupled to the drain of the first transistor M1 and the cathode of the first diode D1 and the other end of the third resistor R3 is coupled to the cathode of the third Zener diode ZD3 and the gate of the third transistor M3. One end of the fourth resistor R4 is coupled to the current source 300, and the other end of the fourth resistor R4 is coupled to the drain of the third transistor M3, the gate of the second transistor M2, and the cathode of the second Zener diode ZD2. The gate of the second transistor M2 and the drain of the third transistor M3 are coupled to the cathode of the second Zener diode ZD2, and the sources of the second transistor M2 and the third transistor M3 are coupled to the anode of the second Zener diode ZD2, the anode of the third Zener diode ZD3 and the output voltage V+.

The third selecting circuit 123 may comprise a third diode D3, a fifth resistor R5, a sixth resistor R6, a fourth Zener diode ZD4, a fifth Zener diode ZD5, a fourth transistor M4 and a fifth transistor M5. One end of the fifth resistor R5 is coupled to the drain of the second transistor M2 and the cathode of the second diode D2, and the other end of the fifth resistor R5 is coupled to the cathode of the fifth Zener diode ZD5 and the gate of the fifth transistor M5. One end of the sixth resistor R6 is coupled to the current source 300, and the other end of the sixth resistor R6 is coupled to the drain of the fifth transistor M5, the gate of the fourth transistor M4, and the cathode of the fourth Zener diode ZD4. The gate of the fourth transistor M4 and the drain of the fifth transistor M5 are coupled to the cathode of the fourth Zener diode ZD4, and the sources of the fourth transistor M4 and the fifth transistor M5 are coupled to the anode of the fourth Zener diode ZD4, the anode of the fifth Zener diode ZD5 and the output voltage V+.

The fourth selecting circuit 124 may comprise a fourth diode D4, a seventh resistor R7, an eighth resistor R8, a sixth Zener diode ZD6, a seventh Zener diode ZD7, a sixth transistor M6 and a seventh transistor M7. One end of the seventh resistor R7 is coupled to the drain of the fourth transistor M4 and the cathode of the third diode D3, and the other end of the seventh resistor R7 is coupled to the cathode of the seventh Zener diode ZD7 and the gate of the seventh transistor M7. One end of the eighth resistor R8 is coupled to the current source 300, and the other end of the eighth resistor R8 is coupled to the drain of the seventh transistor M7, the gate of the sixth transistor M6, and the cathode of the sixth Zener diode ZD6. The gate of the sixth transistor M6 and the drain of the seventh transistor M7 are coupled to the cathode of the sixth Zener diode ZD6, and the sources of the sixth transistor M6 and the seventh transistor M7 are coupled to the anode of the sixth Zener diode ZD6, the anode of the seventh Zener diode ZD7 and the output voltage V+.

The fifth selecting circuit 125 may comprise a fifth diode D5, a ninth resistor R9, a tenth resistor R10, an eighth Zener diode ZD8, a ninth Zener diode ZD9, an eighth transistor M8 and a ninth transistor M9. One end of the ninth resistor R9 is coupled to the drain of the sixth transistor M6 and the cathode of the fourth diode D4, and the other end of the ninth resistor R9 is coupled to the cathode of the ninth Zener diode ZD9 and the gate of the ninth transistor M9. One end of the tenth resistor R10 is coupled to the current source 300, and the other end of the tenth resistor R10 is coupled to the drain of the ninth transistor M9, the gate of the eighth transistor M8, and the cathode of the eighth Zener diode ZD8. The gate of the eighth transistor M8 and the drain of the ninth transistor M9 are coupled to the cathode of the eighth Zener diode ZD8, and the sources of the eighth transistor M8 and the ninth transistor M9 are coupled to the anode of the eighth Zener diode ZD8, the anode of the ninth Zener diode ZD9 and the output voltage V+.

The sixth selecting circuit 126 may comprise a sixth diode D6, an eleventh resistor R11, a twelfth resistor R12, a tenth Zener diode ZD10, a eleventh Zener diode ZD11, a tenth transistor M10 and a eleventh transistor M11. One end of the eleventh resistor R11 is coupled to the drain of the eighth transistor M8 and the cathode of the fifth diode D5, and the other end of the eleventh resistor R11 is coupled to the cathode of the eleventh Zener diode ZD11 and the gate of the eleventh transistor M11. One end of the twelfth resistor R12 is coupled to the current source 300, and the other end of the twelfth resistor R12 is coupled to the drain of the eleventh transistor M11, the gate of the tenth transistor M10, and the cathode of the tenth Zener diode ZD10. The gate of the tenth transistor M10 and the drain of the eleventh transistor M11 are coupled to the cathode of the tenth Zener diode ZD10, and the sources of the tenth transistor M10 and the eleventh transistor M11 are coupled to the anode of the tenth Zener diode ZD10, the anode of the eleventh Zener diode ZD11 and the output voltage V+.

The diodes D1~D6 may be coupled to the drains of the first transistor M1, the second transistor M2, the fourth transistor M4, the sixth transistor M6, the eighth transistor M8 and the tenth transistor M10 respectively (e.g. the first diode D1 is coupled to the drain of the first transistor M1). The Zener diodes ZD1~ZD11 may be coupled to the gates and sources of the transistors M1~M11 (e.g. one end of the first Zener diode ZD1 is coupled to the gate of the first transistor M1 and the other end of the first Zener diode ZD1 is coupled to the source of the first transistor M1) to limit the gate-source voltages $V_{GS}$ of the transistors M1~M11 to protect the transistors M1~M11. According to an embodiment of the disclosure, the transistors M1~M11 may be the Metal-Oxide-Semiconductor Field-Effect Transistors (MOSFETs) or Bipolar Junction Transistors (BJTs), but the disclosure should not be limited thereto. It should be noted that the voltage selecting circuit 120 comprises six stages of the selecting circuits, but the disclosure should not be limited thereto. The number of the selecting circuit can be adjusted based on the number of voltages generated by the boost circuit 110.

In addition, as shown in FIG. 3, the first switch circuit 140 may comprise a first switch S1 and a second switch S2, and the first switch circuit 140 is coupled to the adjustable current source 160; and the second switch circuit 150 may comprise a third switch S3 and a fourth switch S4, and the second switch circuit 150 is coupled to the adjustable current source 160. One end of the first switch S1 may be coupled to the diode Da, and the other end of the first switch S1 may be coupled to the first electrode input end E1. One end of the second switch S2 may be coupled to the second electrode input end E2, and the other end of the second switch S2 may be coupled to the ground. One end of the third switch S3 may be coupled to the diode Db, and the other end of the third switch S3 may be coupled to the second electrode input end E2. One end of the fourth switch S4 may be coupled to the first electrode input end E1, and the other end of the fourth switch S4 may be coupled to the ground. One end of the diode Da may be coupled to the first switch S1 and the other end of the diode Da may be coupled to the voltage selecting circuit 120. One end of the diode Db may be coupled to the third switch S3 and the other end of the diode Db may be coupled to the voltage selecting circuit 120. The control circuit 130 may be configured to control enabling or disabling of the first switch circuit 140 and the second switch circuit 150 to control the transformation between the positive voltage and the negative voltage. When the current flowing through the tissue impedance R is positive current (e.g. the current I1 as shown in FIG. 3), the control circuit 130 may enable the first switch circuit 140 (i.e. enable the first switch S1 and the second switch S2) and disable the second switch circuit 150 (i.e. disable the third switch S3 and the fourth switch S4), and the reference voltage Vrefin generated on the tissue impedance R may be transmitted from the diode Da to the voltage selecting circuit 120. When the current flowing through the tissue impedance R is negative current (e.g. the current I2 as shown in FIG. 3), the control circuit 130 may enable the second switch circuit 150 (i.e. enable the third switch S3 and the fourth switch S4) and disable the first switch circuit 140 (i.e. disable the first switch S1 and the second switch S2), and the reference voltage Vrefin generated on the tissue impedance R may be transmitted from the diode Db to the voltage selecting circuit 120. In addition, the control circuit 130 may control the current generated by the adjustable current source 160. In the embodiment of the disclosure, the first switch circuit 140 and the second switch circuit 150 may be an H-bridge structure. Therefore, the currents of two directions (i.e. positive current and the negative current) can be generated to make the alternating current (AC) voltage can be used for the electrical stimulation. It should be noted that in the embodiment, the first switch circuit 140 and the second switch circuit 150 are an H-bridge structure, but the disclosure should not be limited thereto. In other embodiments, other switch circuit structures which can achieve equivalent effect also can be applied to the first switch circuit 140 and the second switch circuit 150.

In addition, as shown in FIG. 3, the voltage selecting circuit 120 may detect (or obtain) the reference voltage Vrefin generated on the tissue impedance R from the diode Da or the diode Db (i.e. the reference voltage Vrefin may be fed back to the voltage selecting circuit 120 from the tissue impedance R). The voltage selecting circuit 120 may select one of the voltages V1~V6 to be the output voltage V+ in order to adjust the power voltage immediately. The operation of the voltage selecting circuit 120 is illustrated based on FIGS. 4A-4D below.

Figure 4A:
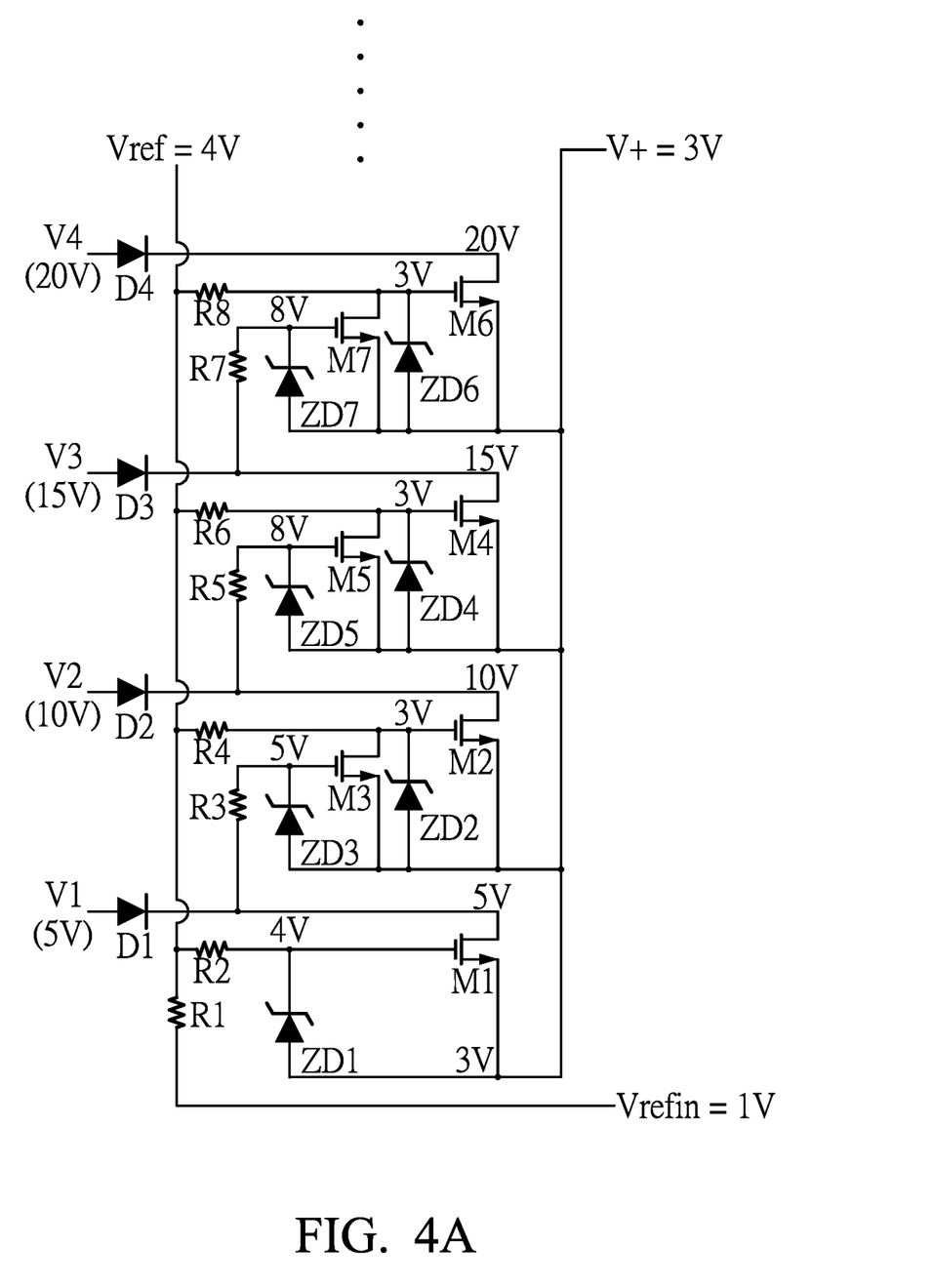
FIG. 4A is a schematic diagram of the voltage selecting circuit 120 generating the output voltage V+ based on the reference voltage Vrefin according to an embodiment of the disclosure.

FIG. 4A is a schematic diagram of the voltage selecting circuit 120 generating the output voltage V+ based on the reference voltage Vrefin according to an embodiment of the disclosure. In the embodiment, it is assumed that the reference voltage Vrefin the voltage selecting circuit 120 detecting (or obtaining) from the diode Da or the diode Db is 1V, and the reference voltage Vrefin is changed to 4V reference voltage Vref after the reference voltage Vrefin passes through the first register R1 and the current source 300. When the reference voltage Vref is 4V, the first diode D1 is forward biased and the first transistor M1 is enabled (i.e. the first transistor M1 is "ON"). Therefore, the voltage V1 (5V) is transmitted by the first diode D1, and after the voltage V1 (5V) passes through the first transistor M1 (the gate voltage is 4V and the drain voltage is 5V), the first transistor M1 may output 3V of output voltage V+. That is to say, in the embodiment, the output voltage V+ is outputted by the first selecting circuit 121. In addition, when the reference voltage Vref is 4V, the second diode D2, the third diode D3 and the fourth diode D4 are forward biased, the third transistor M3 (the gate voltage is 5V), the fifth transistor M5 (the gate voltage is 8V and the drain voltage is 3V) and the seventh transistor M7 (the gate voltage is 8V and the drain voltage is 3V) are enabled/turned on (i.e. the third transistor M3, the fifth transistor M5, and the seventh transistor M7 are "ON"), and the second transistor M2 (the gate voltage is 3V and drain voltage is 10V), the fourth transistor M4 (the gate voltage is 3V and the drain voltage is 15V) and the sixth transistor M6 (the gate voltage is 3V and the drain voltage is 20V) are disabled (i.e. the second transistor M2, the fourth transistor M4 and the sixth transistor M6 are "OFF"). Therefore, voltages V2 (10V), V3 (15V) and V4 (20V) may not be outputted by the second transistor M2, the fourth transistor M4 and the sixth transistor M6 respectively.

Figure 4B:
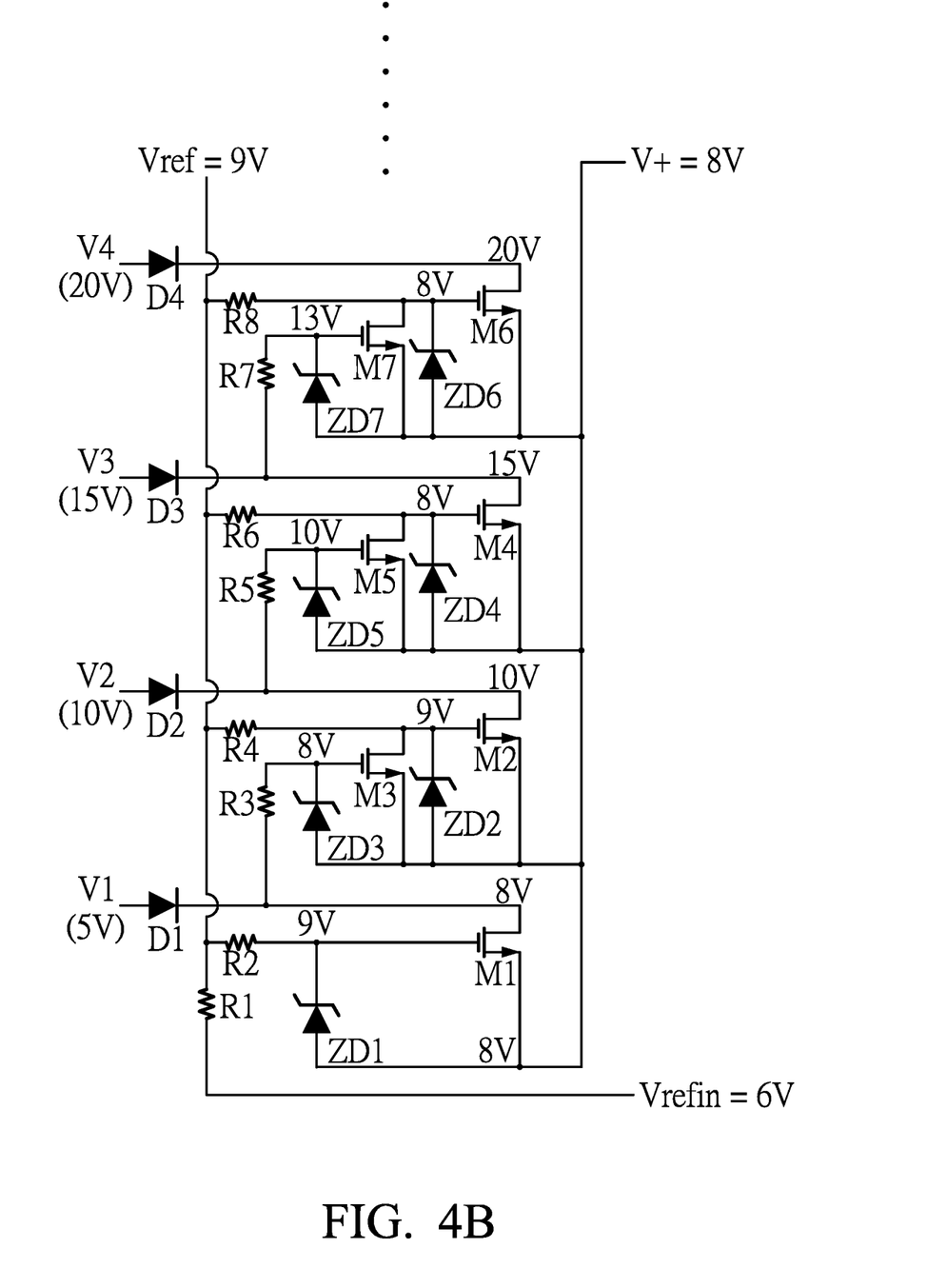
FIG. 4B is a schematic diagram of the voltage selecting circuit 120 generating the output voltage V+ based on the reference voltage Vrefin according to another embodiment of the disclosure.

FIG. 4B is a schematic diagram of the voltage selecting circuit 120 generating the output voltage V+ based on the reference voltage Vrefin according to another embodiment of the disclosure. In the embodiment, it is assumed that the reference voltage Vrefin the voltage selecting circuit 120 detecting (or obtaining) from the diode Da or the diode Db is 6V, and the reference voltage Vrefin is changed to 9V reference voltage Vref after the reference voltage Vrefin passes through the first register R1 and the current source 300. When the reference voltage Vref is 9V, the first diode D1 is reverse biased and the second diode D2 is forward biased. Therefore, the voltage V1 (5V) is not transmitted by the first diode D1 and the voltage V2 (10V) is transmitted by the second diode D2. In addition, when the reference voltage Vref is 9V, the first transistor M1 (the gate voltage is 9V and drain voltage is 8V) and the second transistor M2 (the gate voltage is 9V and drain voltage is 10V) are enabled (i.e. the first transistor M1 and the second transistor M2 are "ON"), and the third transistor M3 (the gate voltage is 8V and the drain voltage is 9V) is disabled/turned off (i.e. the third transistor M3 is "OFF"). Therefore, after the voltage V2 (10V) passes through the second transistor M2, the second transistor M2 may output 8V output voltage V+. That is to say, in the embodiment, the output voltage V+ is outputted by the second selecting circuit 122. In addition, when the reference voltage Vref is 9V, the third diode D3 and the fourth diode D4 are forward biased, the fifth transistor M5 (the gate voltage is 10V and the drain voltage is 8V) and the seventh transistor M7 (the gate voltage is 13V and the drain voltage is 8V) are enabled (i.e. the fifth transistor M5 and the seventh transistor M7 are "ON"), and the fourth transistor M4 (the gate voltage is 8V and the drain voltage is 15V) and the sixth transistor M6 (the gate voltage is 8V and the drain voltage is 20V) are disabled (i.e. the fourth transistor M4 and the sixth transistor M6 are "OFF"). Therefore, voltages V3 (15V) and V4 (20V) may not be outputted by the fourth transistor M4 and the sixth transistor M6 respectively.

Figure 4C:
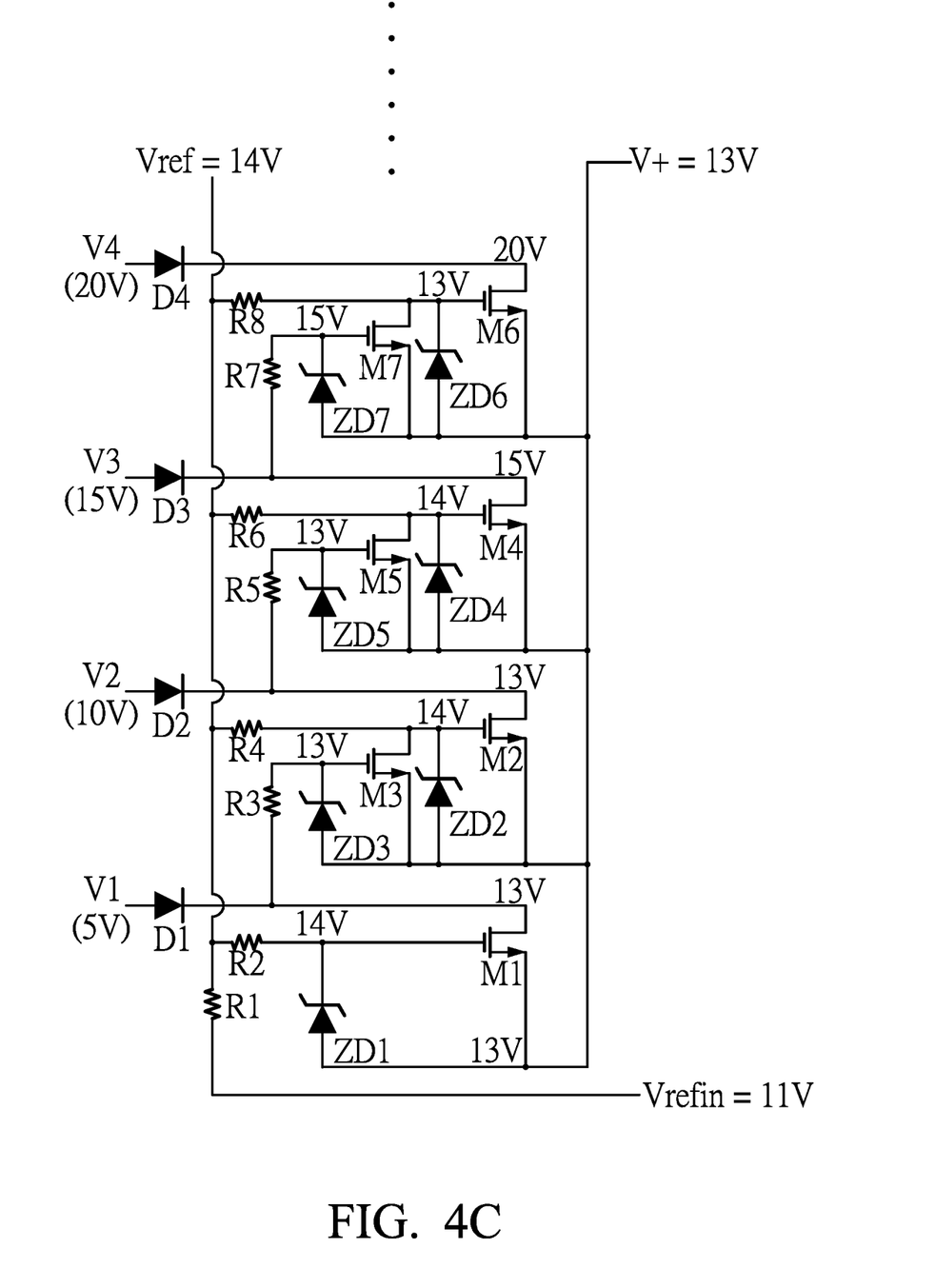
FIG. 4C is a schematic diagram of the voltage selecting circuit 120 generating the output voltage V+ based on the reference voltage Vrefin according to another embodiment of the disclosure.

FIG. 4C is a schematic diagram of the voltage selecting circuit 120 generating the output voltage V+ based on the reference voltage Vrefin according to another embodiment of the disclosure. In the embodiment, it is assumed that the reference voltage Vrefin the voltage selecting circuit 120 detecting (or obtaining) from the diode Da or the diode Db is 11V, and the reference voltage Vrefin is changed to 14V reference voltage Vref after the reference voltage Vrefin passes through the first register R1 and the current source 300. When the reference voltage Vref is 14V, the first diode D1 and second diode D2 are reverse biased and the third diode D3 is forward biased. Therefore, the voltage V1 (5V) and the voltage V2 (10V) are not transmitted by the first diode D1 and the second diode D2 and the voltage V3 (15V) is transmitted by the third diode D3. In addition, when the reference voltage Vref is 14V, the first transistor M1 (the gate voltage is 14V and drain voltage is 13V), the second transistor M2 (the gate voltage is 14V and drain voltage is 13V) and the fourth transistor M4 (the gate voltage is 14V and the drain voltage 15V) are enabled (i.e. the first transistor M1, the second transistor M2 and the fourth transistor M4 are "ON"), and the third transistor M3 (the gate voltage is 13V and the drain voltage is 14V) and the fifth transistor M5 (the gate voltage is 13V and the drain voltage is 14V) are disabled (i.e. the third transistor M3 and the fifth transistor M5 are "OFF"). Therefore, after the voltage V3 (15V) passes through the fourth transistor M4, the fourth transistor M4 may output 13V output voltage V+. That is to say, in the embodiment, the output voltage V+ is outputted by the third selecting circuit 123. In addition, when the reference voltage Vref is 14V, the fourth diode D4 is forward biased, the seventh transistor M7 (the gate voltage is 15V and the drain voltage is 13V) is enabled (i.e. the seventh transistor M7 is "ON"), and the sixth transistor M6 (the gate voltage is 13V and the drain voltage is 20V) is disabled (i.e. the sixth transistor M6 is "OFF"). Therefore, V4 (20V) may not be outputted by the sixth transistor M6.

Figure 4D:
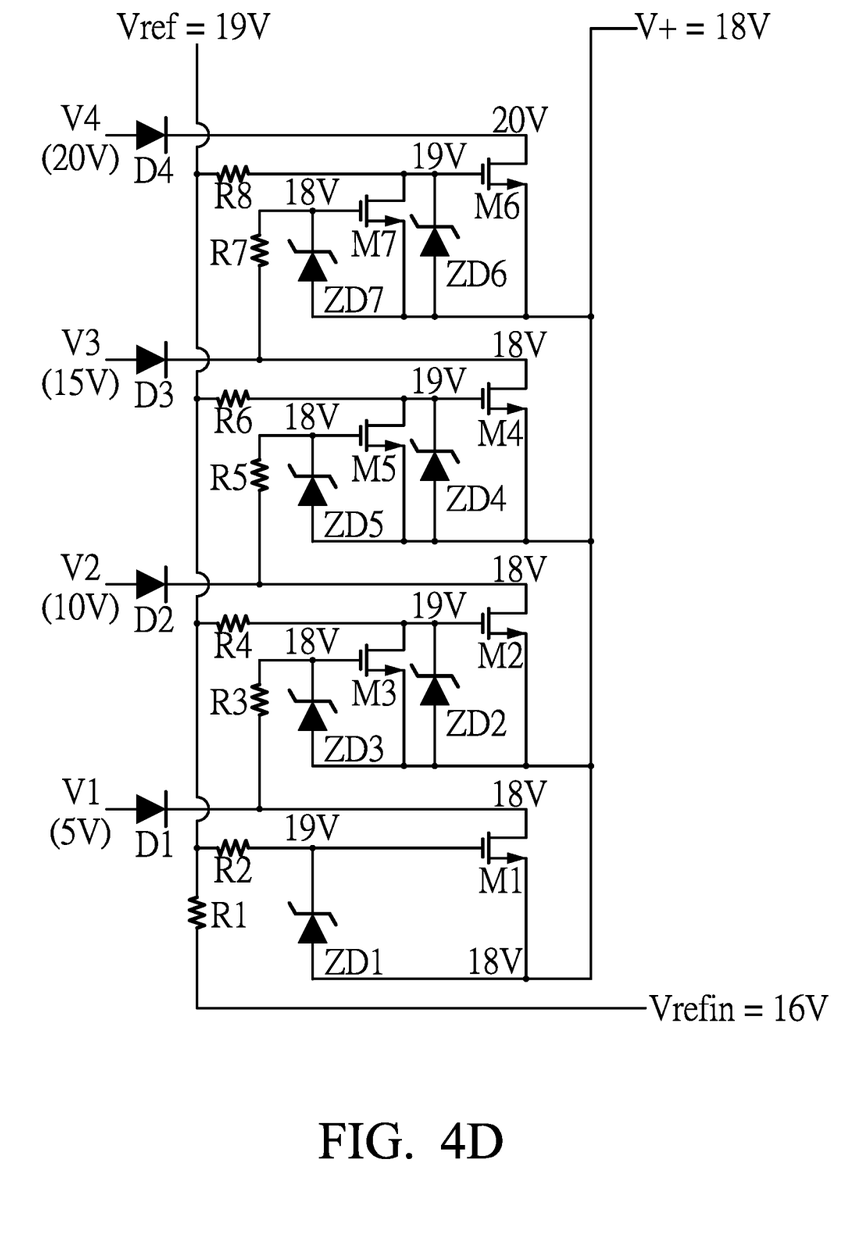
FIG. 4D is a schematic diagram of the voltage selecting circuit 120 generating the output voltage V+ based on the reference voltage Vrefin according to another embodiment of the disclosure.

FIG. 4D is a schematic diagram of the voltage selecting circuit 120 generating the output voltage V+ based on the reference voltage Vrefin according to another embodiment of the disclosure. In the embodiment, it is assumed that the reference voltage Vrefin the voltage selecting circuit 120 detecting (or obtaining) from the diode Da or the diode Db is 16V, and the reference voltage Vrefin is changed to 19V reference voltage Vref after the reference voltage Vrefin passes through the first register R1 and the current source 300. When the reference voltage Vref is 19V, the first diode D1, second diode D2 and the third diode D3 are reverse biased and the fourth diode D4 is forward biased. Therefore, the voltage V1 (5V), voltage V2 (10V) and the voltage V3 (15V) are not transmitted by the first diode D1, the second diode D2 and the third diode D3 and the voltage V4 (20V) is transmitted by the fourth diode D4. In addition, when the reference voltage Vref is 19V, the first transistor M1 (the gate voltage is 19V and drain voltage is 18V), the second transistor M2 (gate voltage is 19V and drain voltage is 18V), the fourth transistor M4 (the gate voltage is 19V and the drain voltage 18V) and the sixth transistor M6 (the gate voltage is 19V and the drain voltage is 20V) are enabled (i.e. the first transistor M1, the second transistor M2, the fourth transistor M4 and the sixth transistor M6 are "ON"), and the third transistor M3 (the gate voltage is 18V and the drain voltage is 19V), the fifth transistor M5 (the gate voltage is 18V and the drain voltage is 19V), and the seventh transistor M7 (the gate voltage is 18V and the drain voltage is 19V) are disabled (i.e. the third transistor M3, the fifth transistor M5 and the seventh transistor M7 are "OFF"). Therefore, after the voltage V4 (20V) passes through the sixth transistor M6, the sixth transistor M4 may output 18V output voltage V+. That is to say, in the embodiment, the output voltage V+ is outputted by the fourth selecting circuit 124.

Accordingly, the voltage selecting circuit 120 may select the output voltage V+ from the voltages V1~V6 based on the reference voltage Vrefin, and the output voltage V+ may be provided to the first switch circuit 140, a second switch circuit 150 and the adjustable current source 160 to provide the electrical stimulation to the tissue impedance R. When the tissue impedance R is changed, the changed reference voltage Vrefin will be fed back to the voltage selecting circuit 120 to select the suitable output voltage V+.

It should be noted that, FIGS. 4A-4B are only used to illustrate the embodiments of the disclosure, but the disclosure should not be limited thereto.

Figure 5:
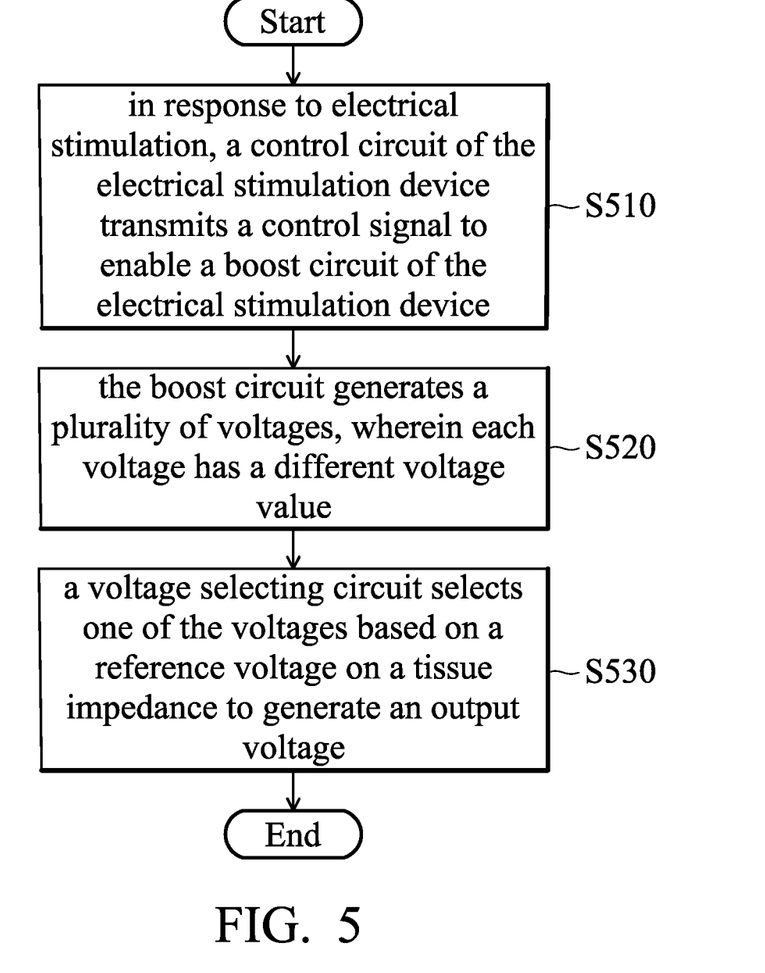
FIG. 5 is a flow chart illustrating an electrical stimulation method according to an embodiment of the disclosure.

FIG. 5 is a flow chart illustrating an electrical stimulation method according to an embodiment of the disclosure. The electrical stimulation method can be applied to the electrical stimulation device 100. As shown in FIG. 5, in step S510, in response to electrical stimulation, a control circuit 130 of the electrical stimulation device 100 may transmit a control signal to enable a boost circuit 110 of the electrical stimulation device 100.

In step S520, the boost circuit 110 of the electrical stimulation device 100 generates a plurality of voltages V1~V6, wherein each of the voltages V1~V6 has a different voltage value.

In step S530, a voltage selecting circuit 120 of the electrical stimulation device 100 may select one of the voltages V1~V6 based on a reference voltage Vrefin generated on a tissue impedance R to generate an output voltage V+.

According to an embodiment of the disclosure, in the electrical stimulation method, the voltage selecting circuit may comprise a plurality of stages of the selecting circuits, wherein the selecting circuits correspond to the voltages generated by the boost circuit respectively. In some embodiments, each stage of the selecting circuit may comprise at least a diode, a first Zener diode and a first transistor. The diode may be coupled to the boost circuit. The first drain of the first transistor may be coupled to the diode, the first source of the first transistor may be coupled to one end of the first Zener diode, and the first gate of the first transistor may be coupled to the other end of the first Zener diode. In some embodiments, except for the first stage, each stage of the selecting circuits may further comprise a second Zener diode and a second transistor. The second source of the second transistor may be coupled to one end of the second Zener diode, and the second gate of the second transistor may be coupled to the other end of the second Zener diode. According to an embodiment of the disclosure, the electrical stimulation method may further comprises that when the diode of a selecting circuit is forward biased, the first transistor is enabled and the second transistor is disabled, the selecting circuit may output the output voltage based on its corresponding voltage.

According to the electrical stimulation device and method of the disclosure, the voltage selecting circuit of the electrical stimulation device can be used to automatically select one voltage from a plurality of voltages based on a reference voltage on the tissue impedance to generate the output voltage. Therefore, in the electrical stimulation device and method of the disclosure, the output voltage can be adjusted immediately to reduce the power consumption of the electrical stimulation device and extend the service life of the electrical stimulation device. In addition, in the electrical stimulation device and method of the disclosure, the structure of the voltage selecting circuit of the electrical stimulation device may not occupy too much space of the electrical stimulation device. Therefore, the volume of the electrical stimulation can be reduced.

Use of ordinal terms such as "first", "second", "third", etc., in the disclosure and claims is for description. It does not by itself connote any order or relationship.

The steps of the method described in connection with the aspects disclosed herein may be embodied directly in hardware, in a software module executed by a processor, or in a combination of the two. A software module (e.g., including executable instructions and related data) and other data may reside in a data memory such as RAM memory, flash memory, ROM memory, EPROM memory, EEPROM memory, registers, a hard disk, a removable disk, a CD-ROM, or any other form of computer-readable storage medium known in the art. A sample storage medium may be coupled to a machine such as, for example, a computer/processor (which may be referred to herein, for convenience, as a "processor") such that the processor can read information (e.g., code) from and write information to the storage medium. A sample storage medium may be integral to the processor. The processor and the storage medium may reside in an ASIC. The ASIC may reside in user equipment. Alternatively, the processor and the storage medium may reside as discrete components in user equipment. Moreover, in some aspects any suitable computer-program product may comprise a computer-readable medium comprising codes relating to one or more of the aspects of the disclosure. In some aspects a computer program product may comprise packaging materials.

The above paragraphs describe many aspects. Obviously, the teaching of the disclosure can be accomplished by many methods, and any specific configurations or functions in the disclosed embodiments only present a representative condition. Those who are skilled in this technology will understand that all of the disclosed aspects in the disclosure can be applied independently or be incorporated.

While the disclosure has been described by way of example and in terms of preferred embodiment, it should be understood that the disclosure is not limited thereto. Those who are skilled in this technology can still make various alterations and modifications without departing from the scope and spirit of this disclosure. Therefore, the scope of the present disclosure shall be defined and protected by the following claims and their equivalents.

What is claimed is:

1. An electrical stimulation device, comprising:
   a boost circuit, generating a plurality of voltages, wherein each of the voltages has a different voltage value;
   a voltage selecting circuit, coupled to the boost circuit and selecting one voltage from among the voltages according to a reference voltage on a tissue impedance to generate an output voltage; and
   a control circuit, coupled to the boost circuit and in response to electrical stimulation, transmitting a control signal to enable the boost circuit,
   wherein the voltage selecting circuit comprises a plurality of stages of selecting circuits, wherein the stages of the selecting circuits correspond to the voltages, respectively,
   wherein each stage of the selecting circuits comprises:
   a diode, coupled to the boost circuit;
   a first Zener diode; and
   a first transistor, wherein a first drain of the first transistor is coupled to the diode, a first source of the first transistor is coupled to one end of the first Zener diode, and a first gate of the first transistor is coupled to the other end of the first Zener diode.

2. The electrical stimulation device of claim 1, further comprising:
   a first switch circuit, comprising a first switch and a second switch, wherein the first switch and the second switch are coupled to a first electrode input end and a second electrode input end respectively; and a second switch circuit, comprising a third switch and a fourth switch, wherein the third switch and the fourth switch are coupled to the first electrode input end and the second electrode input end respectively, and an end of the fourth switch is coupled to ground.

3. The electrical stimulation device of claim 2, wherein the control circuit controls enabling and disabling of the first switch and the second switch to control a transformation between a positive voltage and a negative voltage.

4. The electrical stimulation device of claim 2, wherein the voltage selecting circuit detects the reference voltage through the first electrode input end or the second electrode input end, wherein the first electrode input end is coupled to one end of the tissue impedance and the second electrode input end is coupled to the other end of the tissue impedance.

5. The electrical stimulation device of claim 4, further comprising:
a first diode, coupled to an adjustable current source and the first switch; and
a second diode, coupled to the adjustable current source and the third switch,
wherein when the first switch is enabled, the first diode is coupled to the first electrode input end to transmit the reference voltage to the voltage selecting circuit, and when the third switch is enabled, the second diode is coupled to the second electrode input end to transmit the reference voltage to the voltage selecting circuit.

6. The electrical stimulation device of claim 1, wherein the boost circuit comprises a plurality of stages of charge pump circuits and a plurality of capacitors, wherein the stages of the charge pump circuits generate the plurality of voltages according to the control signal and the capacitors are configured to store the respective voltages.

7. The electrical stimulation device of claim 1, wherein except for a first stage of the selecting circuit, each stage of the selecting circuits further comprises:
a second Zener diode; and
a second transistor, wherein a second source of the second transistor is coupled to one end of the second Zener diode, and a second gate of the second transistor is coupled to the other end of the second Zener diode.

8. The electrical stimulation device of claim 7, wherein the first stage of the selecting circuit further comprises:
a first resistor, wherein one end of the first resistor is coupled to a first diode and a second diode, and the other end of the first resistor is coupled to a current source; and
a second resistor, wherein one end of the second resistor is coupled to the current source, and the other end of the second resistor is coupled to the first Zener diode and the first gate of the first transistor.

9. The electrical stimulation device of claim 7, wherein except for the first stage, each stage of the selecting circuits further comprises:
a first resistor, wherein one end of the first resistor is coupled to the first drain of the first transistor of a prior stage of the selecting circuit and the diode, and the other end of the first resistor is coupled to the second Zener diode and the second gate of the second transistor; and
a second resistor, wherein one end of the second resistor is coupled to a current source, and the other end of the second resistor is coupled to a second drain of the second transistor.

10. The electrical stimulation device of claim 7, wherein the first gate of the first transistor and a second drain of the second transistor are coupled to one end of the first Zener diode, and the first source of the first transistor and the second source of the second transistor are coupled to the other end of the first Zener diode.

11. The electrical stimulation device of claim 7, wherein for each selecting circuit, when the diode is forward biased, the first transistor is enabled and the second transistor is disabled, the selecting circuit outputs the output voltage based on its corresponding voltage.

12. An electrical stimulation method, applied to an electrical stimulation device, comprising:
transmitting, by a control circuit of the electrical stimulation device, a control signal to enable a boost circuit of the electrical stimulation device in response to electrical stimulation;
generating, by the boost circuit, a plurality of voltages, wherein the voltages have different voltage values; and
selecting, by a voltage selecting circuit of the electrical stimulation device, one voltage from among the voltages according to a reference voltage on a tissue impedance to generate an output voltage,
wherein the voltage selecting circuit comprises a plurality of stages of selecting circuits, wherein the stages of the selecting circuits correspond to the voltages, respectively,
wherein each stage of the selecting circuits comprises a diode, a first Zener diode and a first transistor, wherein the diode is coupled to the boost circuit, wherein a first drain of the first transistor is coupled to the diode, a first source of the first transistor is coupled to one end of the first Zener diode, and a first gate of the first transistor is coupled to the other end of the first Zener diode.

13. The electrical stimulation method of claim 12, wherein the electrical stimulation device further comprises a first switch circuit and a second switch circuit, wherein the first switch circuit comprises a first switch and a second switch, wherein the first switch and the second switch are respectively coupled to a first electrode input end and a second electrode input end, and wherein the second switch circuit comprises a third switch and a fourth switch, wherein the third switch and the fourth switch are respectively coupled to the first electrode input end and the second electrode input end, and an end of the fourth switch is coupled to ground.

14. The electrical stimulation method of claim 13, wherein the control circuit controls enabling and disabling of the first switch and the second switch to control a transformation between a positive voltage and a negative voltage.

15. The electrical stimulation method of claim 13, wherein the voltage selecting circuit detects the reference voltage through the first electrode input end or the second electrode input end, wherein the first electrode input end is coupled to one end of the tissue impedance and the second electrode input end is coupled to the other end of the tissue impedance.

16. The electrical stimulation method of claim 15, wherein the electrical stimulation device further comprises a first diode and a second diode, wherein the first diode is coupled to an adjustable current source and the first switch, and the second diode is coupled to the adjustable current source and the third switch, wherein when the first switch is enabled, the first diode is coupled to the first electrode input end to transmit the reference voltage to the voltage selecting circuit, and when the third switch is enabled, the second diode is coupled to the second electrode input end to transmit the reference voltage to the voltage selecting circuit.

17. The electrical stimulation method of claim 12, wherein the boost circuit comprises a plurality of stages of charge pump circuits and a plurality of capacitors, wherein the stages of the charge pump circuits generate voltages according to the control signal and the capacitors are configured to store the respective voltages.

18. The electrical stimulation method of claim 12, wherein except for a first stage of the selecting circuit, each stage of the selecting circuits further comprises a second Zener diode and a second transistor, wherein a second source of the second transistor is coupled to one end of the second Zener diode, and a second gate of the second transistor is coupled to the other end of the second Zener diode.

19. The electrical stimulation method of claim 18, wherein the first stage of the selecting circuit further comprises a first resistor and a second resistor, wherein one end of the first resistor is coupled to a first diode and a second diode, and the other end of the first resistor is coupled to a current source, and one end of the second resistor is coupled to the current source, and the other end of the second resistor is coupled to the first Zener diode and the first gate of the first transistor.

20. The electrical stimulation method of claim 18, wherein except for the first stage, each stage of the selecting circuits further comprises a first resistor and a second resistor, wherein one end of the first resistor is coupled to the first drain of the first transistor of a prior stage of the selecting circuit and the diode, and the other end of the first resistor is coupled to the second Zener diode and the second gate of the second transistor, and one end of the second resistor is coupled to a current source, and the other end of the second resistor is coupled to a second drain of the second transistor.

21. The electrical stimulation method of claim 18, wherein the first gate of the first transistor and a second drain of the second transistor are coupled to one end of the first Zener diode, and the first source of the first transistor and the second source of the second transistor are coupled to the other end of the first Zener diode.

22. The electrical stimulation method of claim 18, further comprising:

for each selecting circuit, when the diode is forward biased, the first transistor is enabled, and the second transistor is disabled, outputting, by the selecting circuit, the output voltage based on its corresponding voltage.

\* \* \* \* \*